US006303760B1

(12) United States Patent
Dorn et al.

(10) Patent No.: US 6,303,760 B1
(45) Date of Patent: Oct. 16, 2001

(54) ENDOHEDRAL METALLOFULLERENES AND METHOD FOR MAKING THE SAME

(75) Inventors: Harry C. Dorn; Steven A. Stevenson, both of Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 09/458,289

(22) Filed: Dec. 10, 1999

Related U.S. Application Data

(60) Provisional application No. 60/148,209, filed on Aug. 12, 1999.

(51) Int. Cl.[7] .................... C07F 5/00; C07F 7/22; C01F 1/00; C01B 31/00
(52) U.S. Cl. .................... 534/11; 534/15; 556/1; 556/28; 505/460; 423/445 B
(58) Field of Search ............ 423/445 B; 534/11, 534/15; 556/1, 28; 505/460

(56) References Cited

U.S. PATENT DOCUMENTS

| | | | |
|---|---|---|---|
| 5,196,396 | 3/1993 | Lieber | 505/1 |
| 5,288,342 | 2/1994 | Job | 148/320 |
| 5,300,203 | 4/1994 | Smalley | 204/157.41 |
| 5,324,495 | 6/1994 | Gorum | 423/439 |
| 5,348,936 | 9/1994 | McCauley, Jr. et al. | 505/460 |
| 5,472,749 | 12/1995 | Dravid et al. | 427/580 |
| 5,523,438 | 6/1996 | Schlögl et al. | 556/136 |
| 5,547,748 | 8/1996 | Ruoff et al. | 428/323 |
| 5,558,903 | 9/1996 | Bhushan et al. | 427/11 |
| 5,869,626 | 2/1999 | Yamamoto et al. | 534/10 |
| 5,951,832 | 9/1999 | Tanaka et al. | 204/157.47 |

Primary Examiner—Porfirio Nazario-Gonzalez
(74) Attorney, Agent, or Firm—McGuireWoods, LLP

(57) ABSTRACT

A family of trimetallic nitride endohedral metallofullerenes and their preparation are described. The trimetallic nitride endohedral metallofullerenes have the general formula $A_{3-n}X_n@C_m$ where n ranges from 0 to 3, A and X may be trivalent metals and may be either rare earth metal or group IIIB metals, and m is between about 60 and about 200. Further, the $A_{3-n}X_n@C_{68}$, $A_{3-n}X_n@C_{78}$, $A_{3-n}X_n@C_{80}$ families of endohedral fullerenes are described. The trimetallic nitride endohedral metallofullerenes are produced by charging a reactor with a cored graphite rod that has been filled with a metal oxide graphite mixture. The metal oxides correspond to the metals for A and X. The graphite rod is arc discharged in a helium and nitrogen atmosphere to produce the desired trimetallic nitride endohedral metallofullerenes.

39 Claims, 14 Drawing Sheets

Sc₃N

ErSc₂N

Er₂ScN

Er₃N

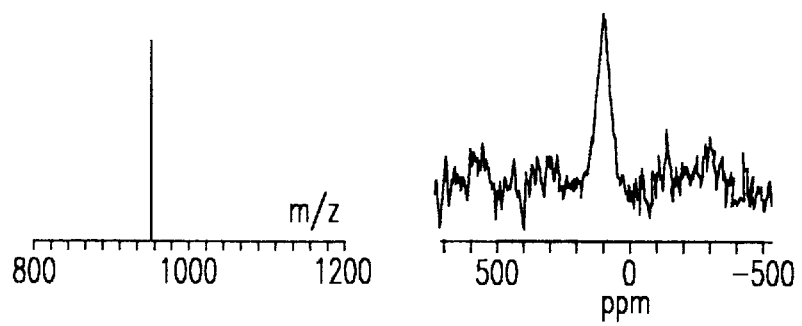
FIG. 10A
FIG. 10B
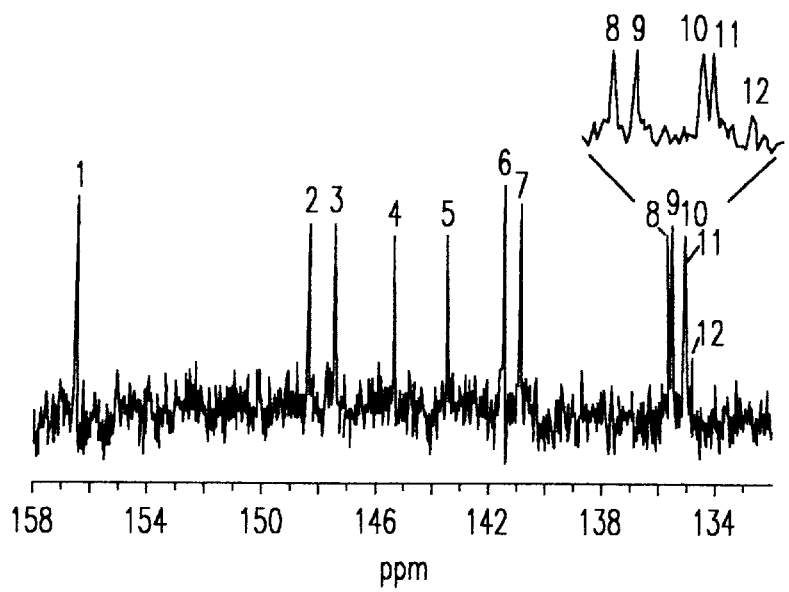
FIG. 10C
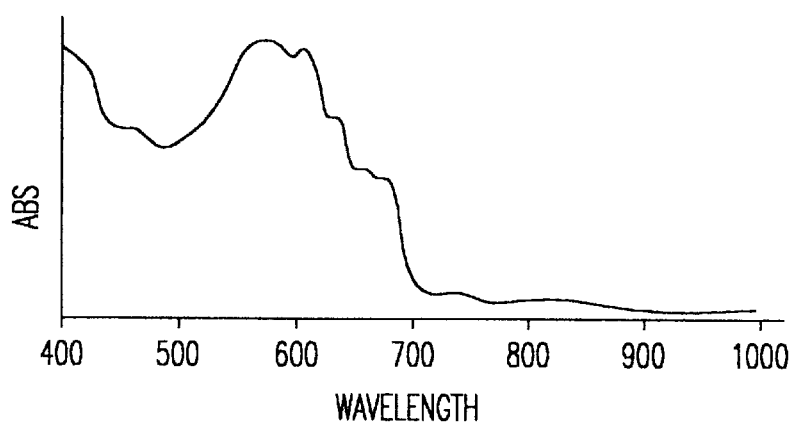
FIG. 10D

ENDOHEDRAL METALLOFULLERENES AND METHOD FOR MAKING THE SAME

This Application claims the benefit of U.S. Provisional Application No. 60/148,209, filed Aug. 12, 1999, herein incorporated by reference in its entirety.

BACKGROUND OF THE INVENTION

The present invention is directed to an endohedral metallofullerene and a method for the making the same. More particularly the present invention is directed to a trimetallic nitride endohedral metallofullerene and a method for making the same.

Fullerenes are a family of closed-caged molecules made up of carbon atoms. The closed-caged molecules consist of a series of five and six member carbon rings. The fullerene molecules can contain 500 or more carbon atoms. The most common fullerene is the spherical $C_{60}$ molecule taking on the familiar shape of a soccer ball.

Fullerenes are typically produced by an arc discharge method using a carbon rod as one or both of the electrodes in a Krätschmer-Huffman generator. Krätschmer, W. et al., Chem. Phys. Lett., 170, 167–170 (1990) herein incorporated by reference in its entirety. Typically the generator has a reaction chamber and two electrodes. The reaction chamber is evacuated and an inert gas is introduced in the reaction chamber at a controlled pressure. A potential is applied between the electrodes in the chamber to produce an arc discharge. The arc discharge forms a carbon plasma in which fullerenes of various sizes are produced.

Many derivatives of fullerenes have been prepared including encapsulating metals inside the fullerene cage. Metal encapsulated fullerenes are typically prepared by packing a cored graphite rod with the metal oxide of the metal to be encapsulated in the fullerene cage. The packed graphite rod is placed in the generator and arc discharged to produce fullerene products. The formation of metal encapsulated fullerences is a complicated process and typically yields only very small amounts of the metal fullerenes.

Fullerenes and their derivatives are useful as superconductor materials, catalysts, and nonlinear optical materials. Fullerene compounds can also find utility as molecular carriers for drugs or catalysts. Fullerenes containing radioactive metals can be useful in missile therapy for cancer and as a radionuclide tracer.

SUMMARY OF THE INVENTION

The present invention is directed to a family of endohedral metallofullerenes having the formula $A_{3-n}X_nN@C_m$ (n=0–3). Further the present invention is directed to the formation of endohedral metallofullerenes by a trimetallic nitride template process ("TNT").

Accordingly, the present invention is directed to an endohedral metallofullerene having the formula $A_{3-n}X_nN@C_m$ wherein A is a metal, X is a second trivalent metal, n is an integer from 0 to 3, and m is an even integer from about 60 to about 200. The integer m may take on values ranging from about 60 to about 100. Typically, m is about 68, 78, or 80. Further, x may be a trivalent metal and has an ionic radius below about 0.095 nm, and A is a trivalent metal having an ionic radius below about 0.095 nm.

In accordance with the present invention, A may be an element selected from the group consisting of a rare earth element and a group IIIB element. Further, A may be selected from the group consisting of Scandium, Yttrium, Lanthanum, Gadolinium, Holmium, Erbium, Thulium, and Ytterbium. X may be an element selected from the group consisting of a rare earth element and a group IIIB element. Still further, X may be selected from the group consisting of Scandium, Yttrium, Lanthanum, Gadolinium, Holmium, Erbium, Thulium, and Ytterbium.

The present invention also includes a method for making a trimetallic nitride endohedral metallofullerene. The method includes charging a reactor with a first metal, carbon, and nitrogen; and reacting the nitrogen, the first metal, and the carbon in the reactor to form an endohedral metallofullerene. The nitrogen may be introduced in the reactor in the form of nitrogen gas and the first metal and carbon are introduced in the reactor in the form of a rod filled with a mixture of a first metal oxide and graphite wherein the first metal oxide is an oxide of the first metal.

The first metal is selected from the group consisting of a rare earth element and a group IIIB element. Typically, the first metal is selected from the group consisting of Scandium, Yttrium, Lanthanum, Gadolinium, Holmium, Erbium, Thulium, and Ytterbium. The first metal may have an ionic radius below about 0.095 nm. Further, the first metal may be a trivalent metal.

The mixture comprises from about 1% to about 5% first metal oxide by weight. Typically the mixture comprises about 3% first metal oxide by weight.

The method further includes reacting the nitrogen, carbon, and first metal further comprises vaporizing the carbon and the first metal in the presence of the nitrogen. The nitrogen may be introduced in the reactor in the form of a carbon nitride or a metal nitride wherein the metal nitride contains the metal to be encapsulated in the fullerene cage.

Still further the method includes adding from about 1 to about 450 mg of cobalt oxide to the mixture of metal oxide and graphite. Typically, the mixture comprises from about 75 to about 225 mg of cobalt oxide.

The method further includes charging the reactor with a first metal, a second metal, carbon and nitrogen and reacting the second metal, the first metal, carbon, and nitrogen to produce the endohedral metallofullerene. In accordance with the present invention, the nitrogen may be introduced in the reactor in the form of nitrogen gas; and the first metal, the second metal, and the carbon are introduced in the reactor in the form of a rod filled with a mixture of a first metal oxide, a second metal oxide, and graphite wherein the first metal oxide is an oxide of the first metal and the second metal oxide is an oxide of the second metal.

The first metal is selected from the group consisting of a rare earth element and a group IIIB element; and the second metal is selected from the group consisting of a rare earth element and a group IIIB element. Typically, the first metal is selected from the group consisting of Scandium, Yttrium, Lanthanum, Gadolinium, Holmium, Erbium, Thulium, and Ytterbium; and the second metal is selected from the group consisting of Scandium, Yttrium, Lanthanum, Gadolinium, Holmium, Erbium, Thulium, and Ytterbium. Further, the first and second metals may have an ionic radius below about 0.095 nm. Still further, the first and second metal may be trivalent metals.

The method includes a mixture having from about 1% to about 5% first metal oxide by weight and from about 1% to about 5% second metal oxide by weight. Typically, the mixture has about 3% first metal oxide and about 2% second metal oxide by weight.

The method further includes reacting the nitrogen, carbon, first metal and second metal further comprises vaporizing the carbon, first metal and second metal in the presence of the nitrogen. The nitrogen may be introduced in the reactor in the form of a carbon nitride or a metal nitride wherein the metal nitride contains the metal to be encapsulated in the fullerene cage.

The mixture may have from about 1 to about 450 mg of cobalt oxide. Typically the mixture has about 75 to about 225 mg of cobalt oxide.

BRIEF DESCRIPTION OF THE DRAWINGS

FIG. 1 a) is a pictorial representation of the structure for an empty cage $C_{80}$ fullerene;

b) is a pictorial representation of the structure for $Sc_3N@C_{80}$;

c) is the NI-DCI mass spectrum for purified $Sc_3N@C_{80}$;

d) is the 150 MHz $^{13}C$ NMR spectrum for purified $^{13}C$ labeled $Sc_3N@C_{80}$ in $CS_2/Cr(acac)_3$.

e) is the UV-Vis-NIR spectrum for $Sc_3N@C_{80}$ in $CS_2$ with an inset showing vertical expansion; and f) is the x-ray photo-electron spectrum (XPS) evaporated on a Au film for $Sc_3N@C_{80}$.

Figure 2:
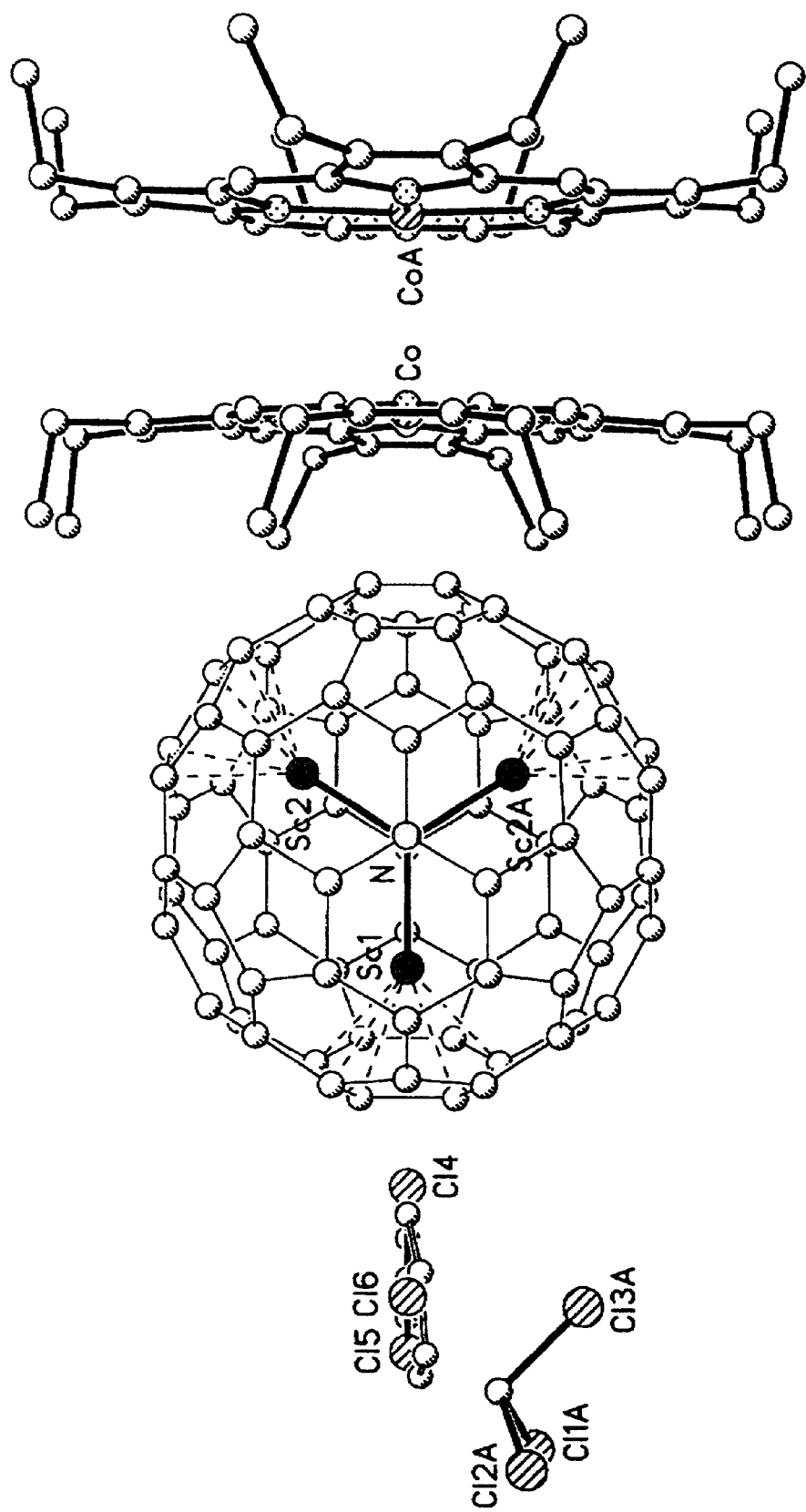

FIG. 2 is the x-ray crystal structure for $Sc_3N@C_{80}$. Also shown are the $Co^{II}(OEP)$—1.5 chloroform—0.5 benzene molecules in the crystal.

FIG. 3 a) is the NI-DCI mass spectrum for the mixed scandium and erbium endohedral metallofullerenes;

b) is a pictorial cut out representation of the structure for $Sc_3N@C_{80}$, $Sc_2ErN@C_{80}$, $ScEr_2N@C_{80}$, and $Er_3N@C_{80}$; and c) is a plot showing the yield enhancements for $Er_xSc_{3-x}N@C_{80}$ (x=0–3) compared to $Sc_3@C_{82}$. The yield enhancements were determined by NI-DCI mass spectrometry. Illustrated are yield enhancements for two different metal loadings, ($Er_2O_3/Sc_2O_3$/powdered graphite, 1.5/1.5/97 w/w—lower circles, and 3/3/94 w/w—upper squares.

FIG. 4 a) is a pictorial representation of the structure of $Y_3N@C_{80}$; and b) is a pictorial slice representation of $A_3N@C_{80}$ showing a range of atomic radii from 0.10–0.075 nm.

Figure 5:
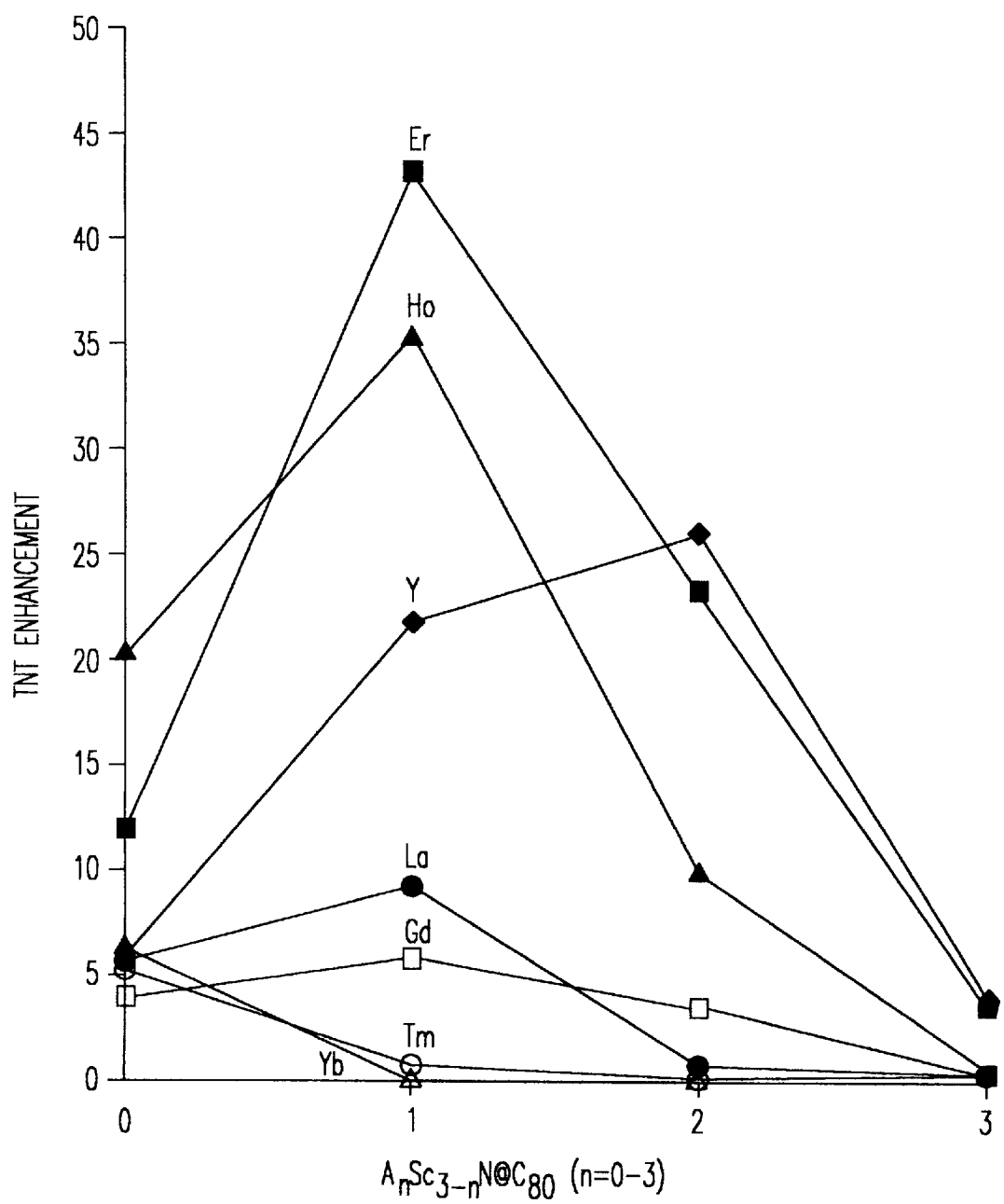

FIG. 5 is a plot showing the yield enhancements for $A_{3-n}Sc_nN@C_{80}$ (n=0–3) compared to $Sc_2@C_{84}$. The yield enhancements were determined by NI-DCI mass spectrometry.

Figure 6:
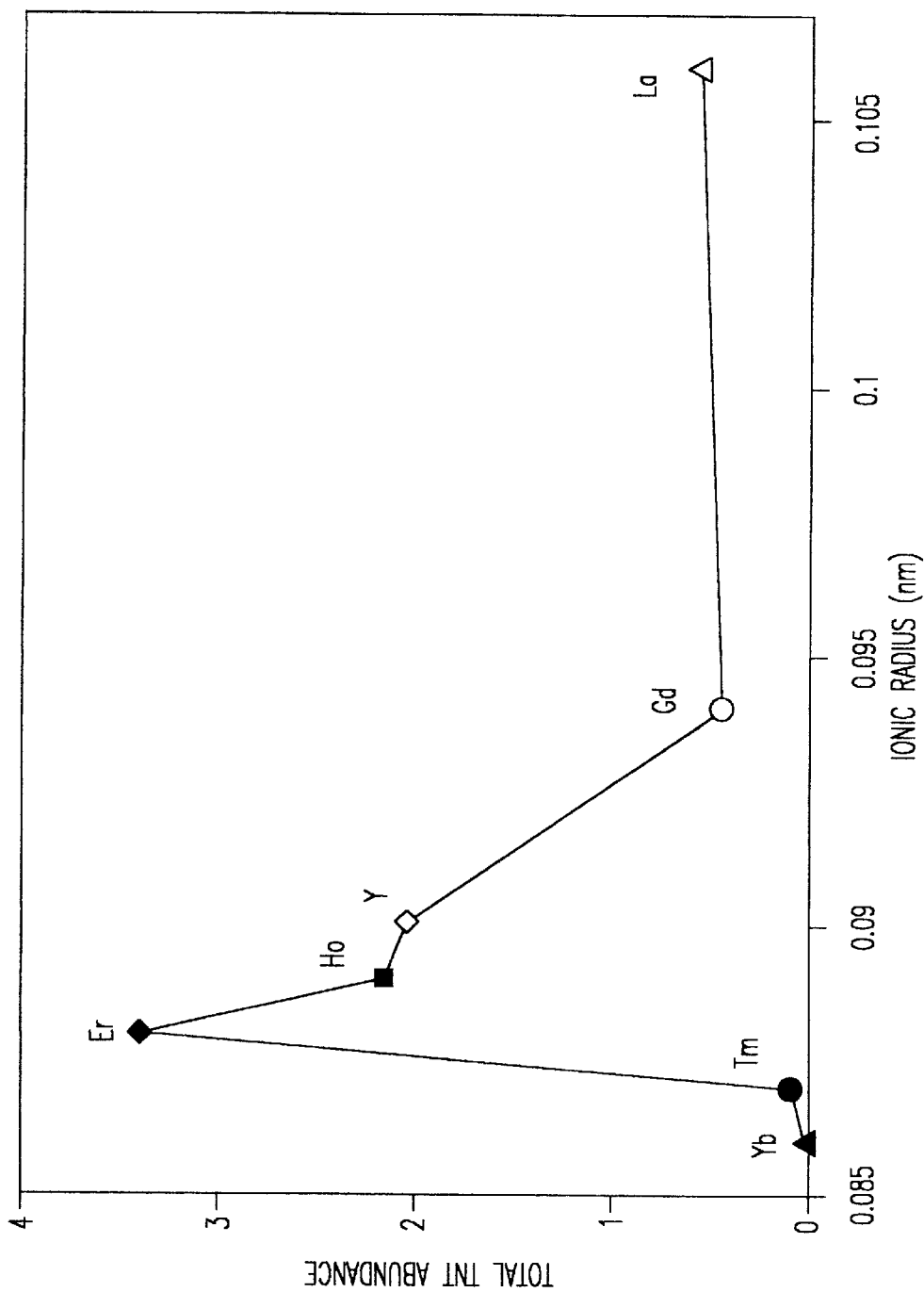

FIG. 6 is a plot showing the total yield for a given metal family $A_{3-n}Sc_nN@C_{80}$ (n=0–2) relative to the empty cage $C_{84}$. The total yield is plotted versus metal (A) ionic radii.

Figure 7:
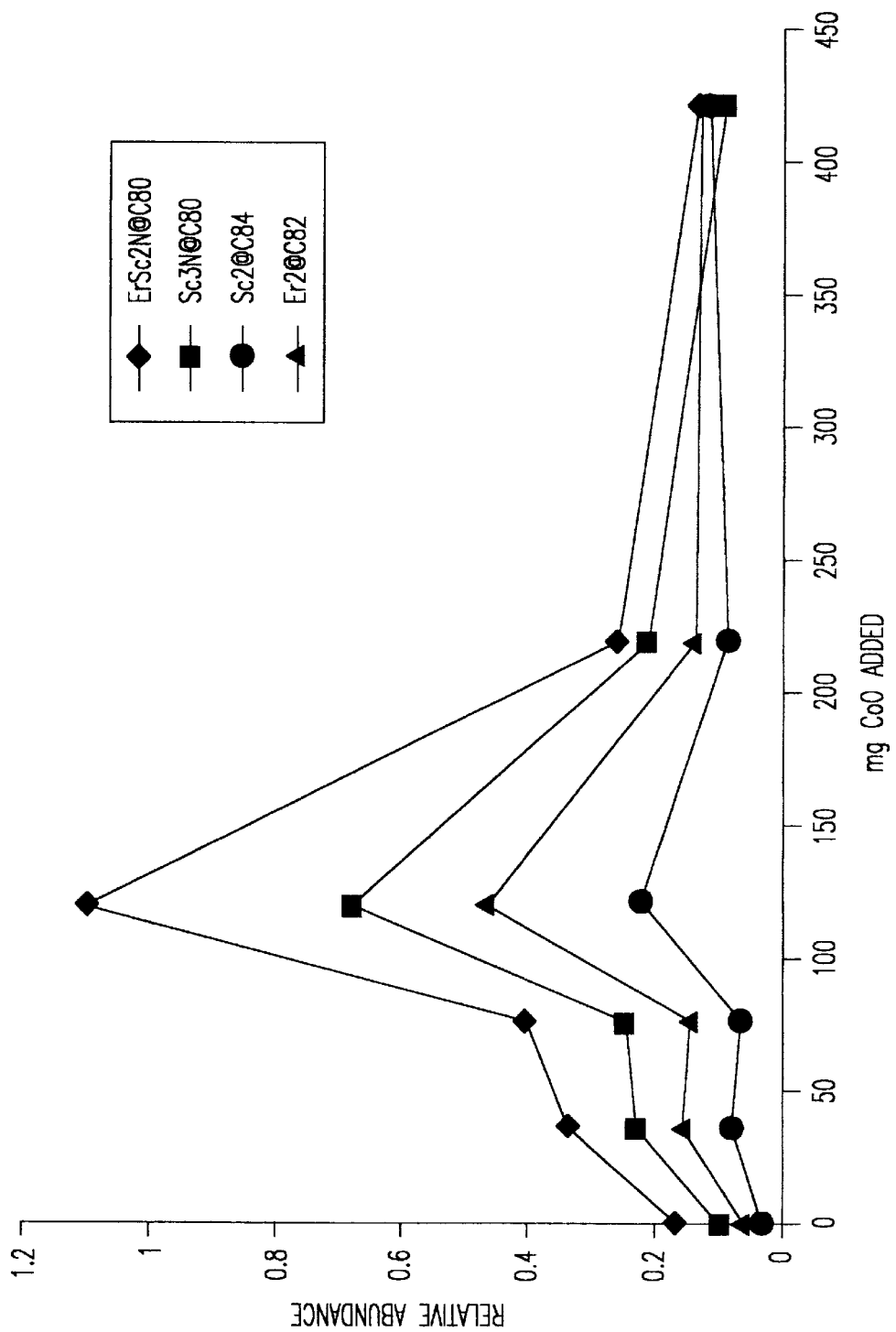
Figure 8A:
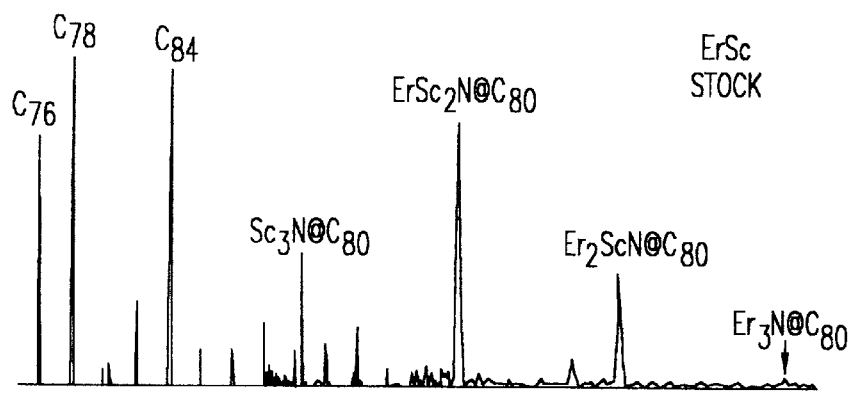
Figure 8B:
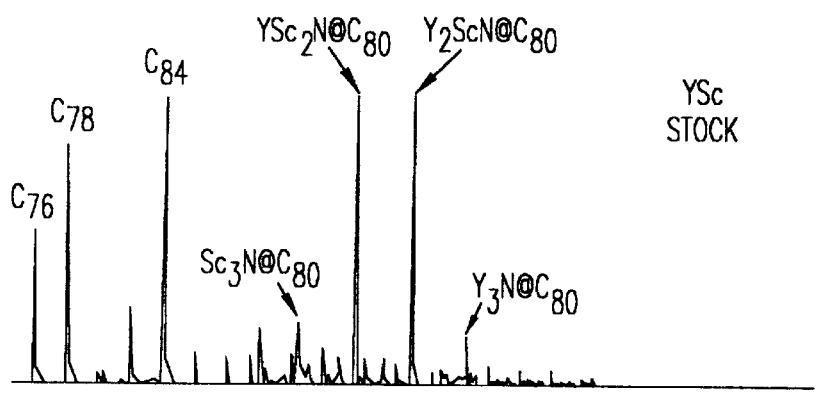
Figure 8C:
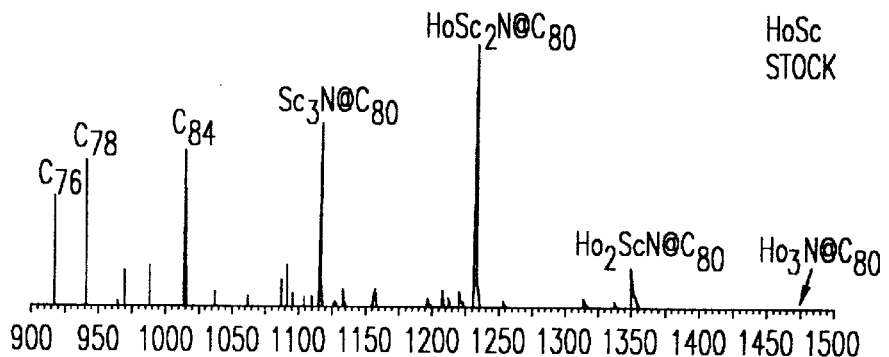
Figure 8D:
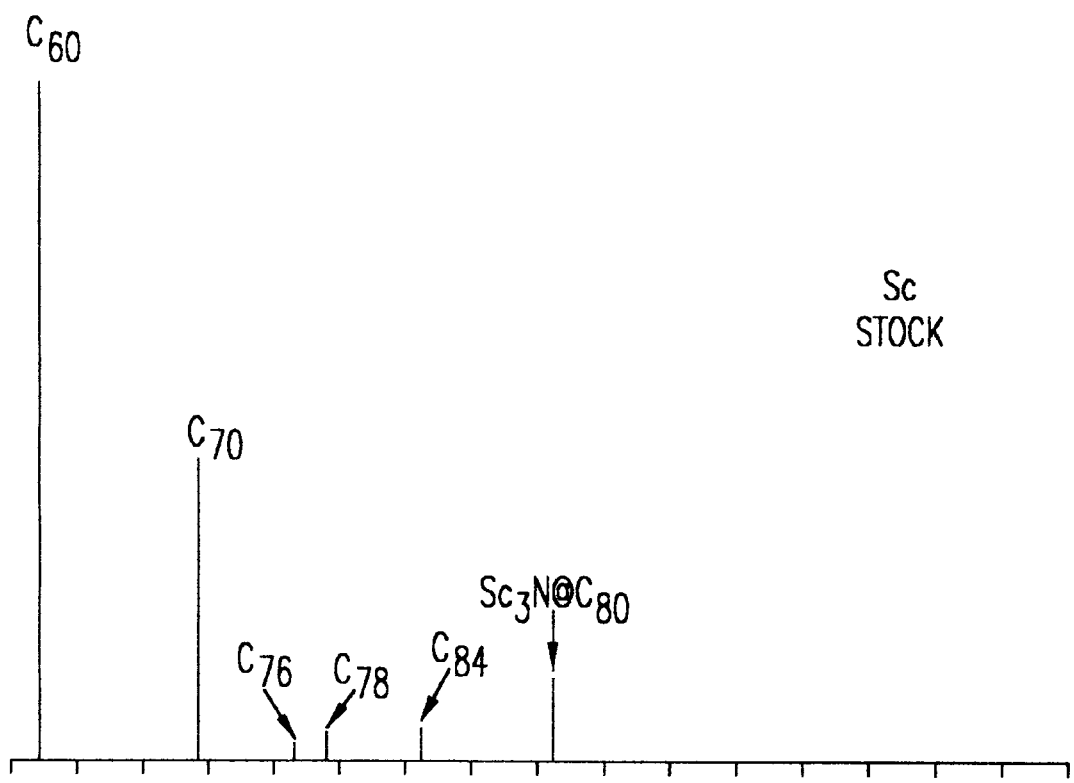

FIG. 7 is a plot showing the effect of $Er_{3-n}Sc_nN@C_{80}$ formation as a function of mg of cobalt oxide added to the mixture in the graphite rods.

FIG. 8 a) is the NI-DCI mass spectrum showing the presence of all $Er_{3-n}Sc_nN@C_{80}$ (n=0–3) family members generated from a $Er_2O_3/Sc_2O_3$ packed graphite rod;

b) is the NI-DCI mass spectrum showing the presence of all $Y_{3-n}Sc_nN@C_{80}$ (n=0–3) family members generated from a $Y_2O_3/Sc_2O_3$ packed graphite rod;

c) is the NI-DCI mass spectrum showing the presence of all $Ho_{3-n}Sc_nN@C_{80}$ (n=0–3) family members generated from a $Ho_2O_3/Sc_2O_3$ packed graphite rod; and d) is the NI-DCI mass spectrum showing the formation of $Sc_3N@C_{80}$ generated from $SC_2O_3$ packed graphite rod.

FIG. 9 a) is a plot showing the yields obtained from mass spectral data for $ASc_2N@C_{68}$ referenced to $Sc_3N@C_{68}$ where A is Yb, Tm, Er, Ho, Y, Gd, and La; and b) is a plot showing the yields obtained from mass spectral data for $A_2Sc_2N@C_{68}$ referenced to $Sc_3N@C_{68}$ where A is Yb, Tm, Er, Ho, Y, Gd, and La.

FIG. 10 a) is the NI-DCI mass spectrum for purified $Sc_3N@C_{68}$;

b) is the 121.5 MHz $^{45}Sc$ NMR spectrum for $Sc_3N@C_{68}$ in $CS_2$ (130,000 scans, 9 hrs, referenced to $ScCl_3$;

c) is the 150 MHz $^{13}C$ NMR spectrum for purified $Sc_3N@C_{68}$ in $CS_2/Cr(acac)$; and d) is the UV-Vis-NIR spectrum for $Sc_3N@C_{68}$ in $CS_2$.

Figure 11:
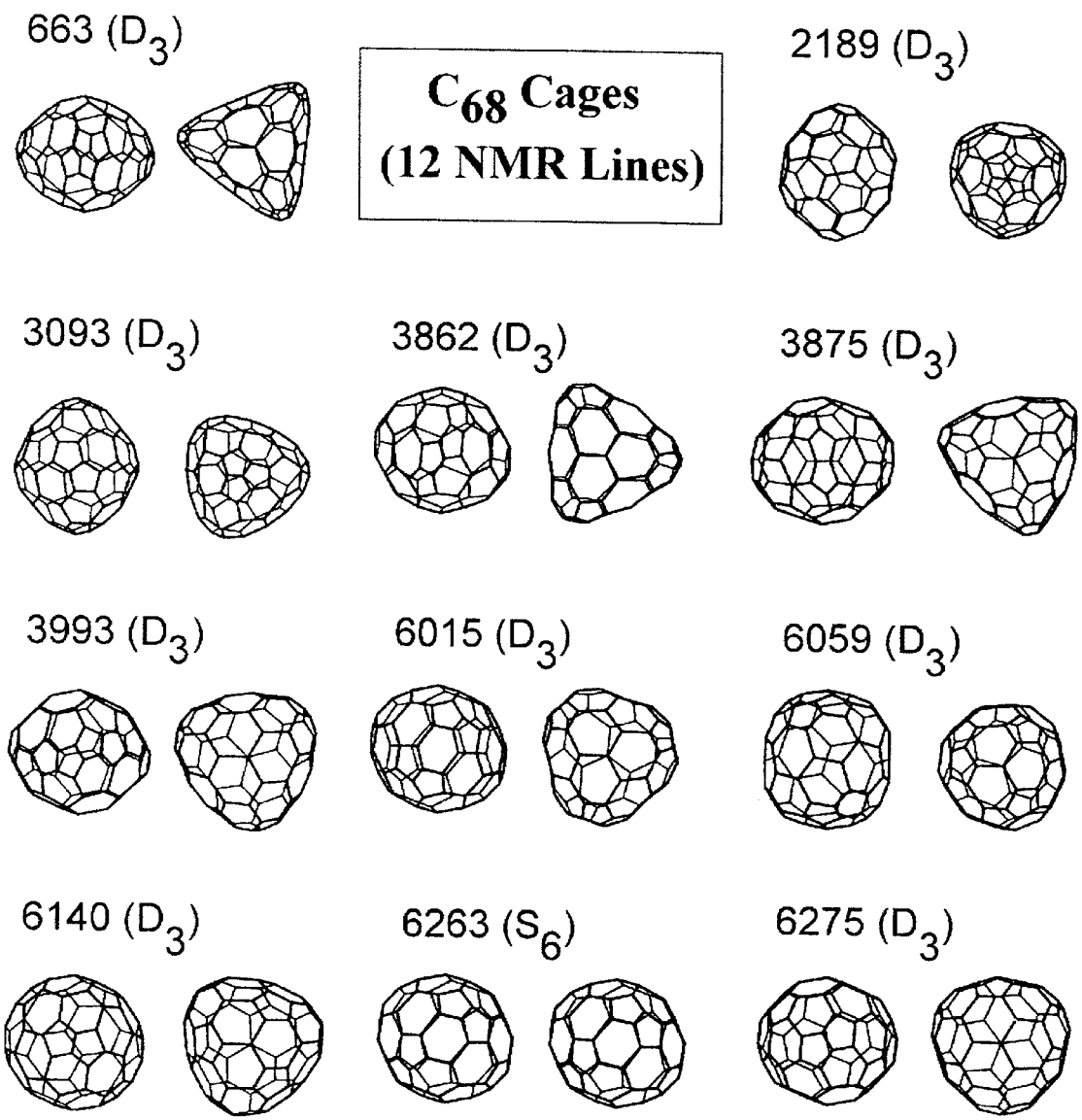

FIG. 11 shows all $C_{68}$ cages generated from the spiral algorithm program having either $D_3$ or $S_6$ symmetry, 12 $^3C$ NMR lines (11×6, 1×2).

Figure 12A:
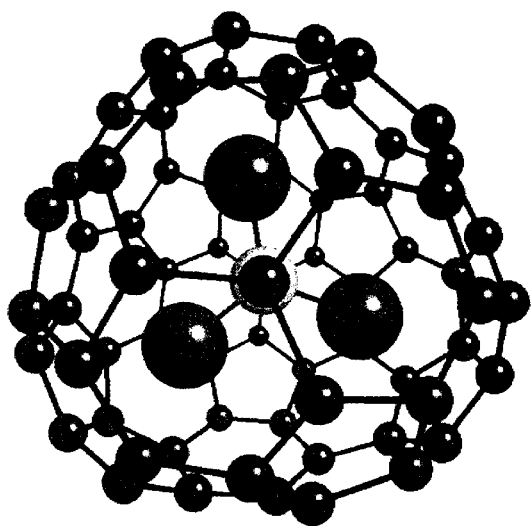
Figure 12B:
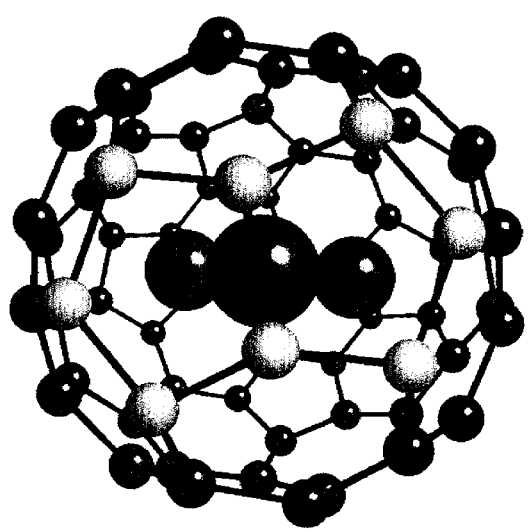

FIG. 12 shows the $Sc_3N@C_{68}$ structure generated from isomer 6140 geometry (DFTB computation level) with encapsulation of the $Sc_3N$ cluster viewed from a) the $C_3$ axis, and b) the $C_2$ axis.

DESCRIPTION OF THE PREFERRED EMBODIMENTS

The present invention is directed to a trimetallic nitride endohedral metallofullerene and a method for making the same. In accordance with the present invention, larger yields of endohedral metallofullerenes are realized when compared to the non-nitride trimetallic endohedral metallofullerenes.

As used herein, "endohedral" refers to the encapsulation of atoms inside the fullerene cage network. Accepted symbols for elements and subscripts to denote numbers of elements are used herein. Further, all elements to the right of an @ symbol are part of the fullerene cage network, while all elements listed to the left are contained within the fullerene cage network. Under this notation, $Sc_3N@C_{80}$ indicates that the $Sc_3N$ trimetallic nitride is situated within a $C_{80}$ fullerene cage.

The present invention is directed to a family of endohedral metallofullerenes representative generally as $A_{3-n}X_nN@C_m$ (n=0–3) where A and X are metal atoms and m can take on even values between about 60 and about 200. To form a trimetallic endohedral metallofullerene having a cage size between about 68 carbon atoms and about 80 carbon atoms, the metal atoms are preferably trivalent and have an ionic radius below about 0.095 nm. When m is about 68, the metal atoms preferably have an ionic radius below about 0.090 nm for the $A_3N$ endohedral species. For the $AX_2N$ and $A_2XN$ endohedral species, the larger atomic radius of 0.095 nm for A can be accommodated as shown in FIG. 9. As the size of the cage increases, the ionic radius for the metal may increase. Further, A and X may be a rare earth element, a group IIIB element, or the like. Preferably, A or X may be Scandium, Yttrium, Lanthanum, Gadolinium, Holmium, Erbium, Thulium, and Ytterbium.

Figure 1:
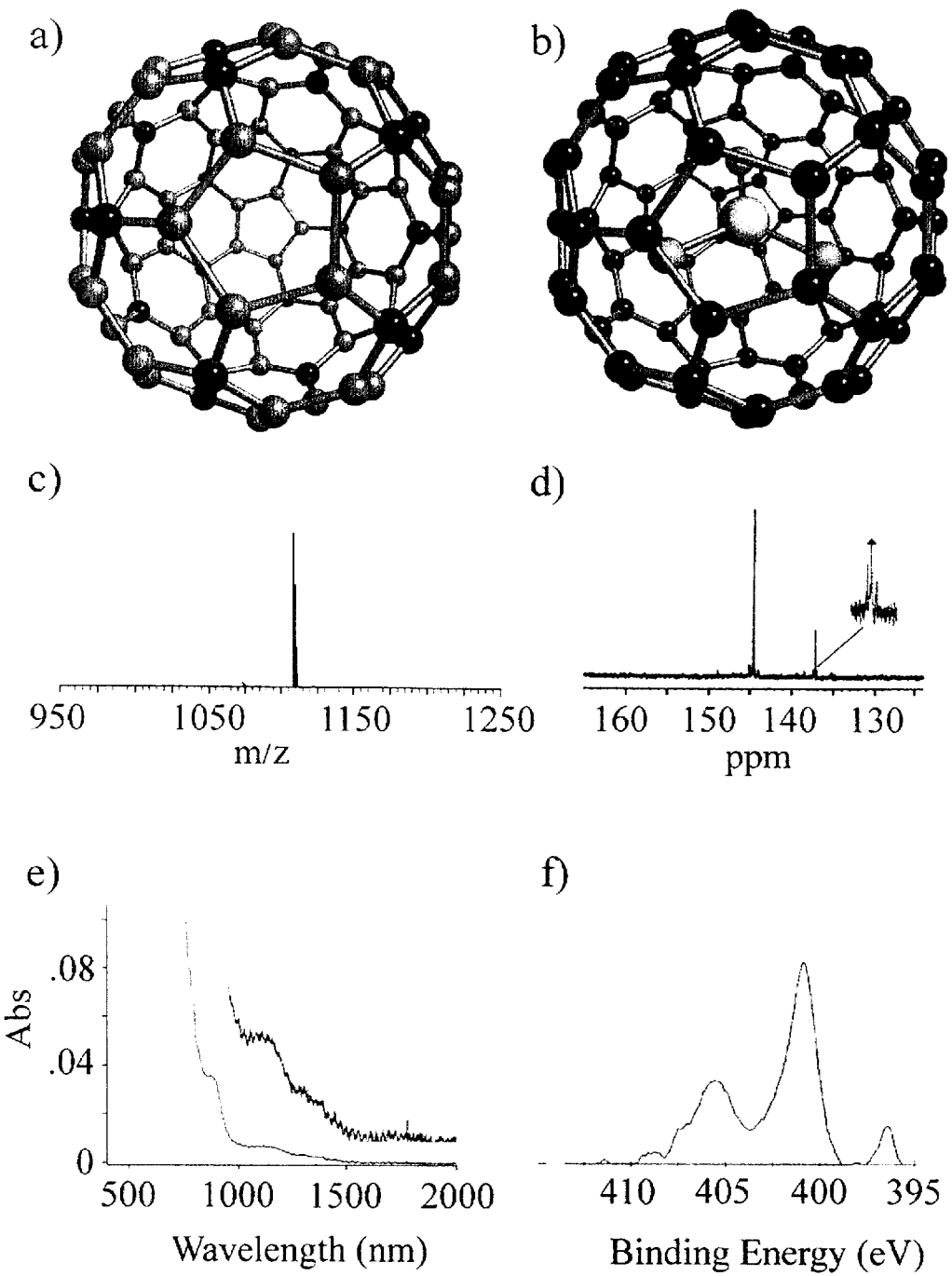

With reference now to FIG. 1, the x-ray crystal structure for $Sc_3NC_{80}$ is shown. The structure in FIG. 1 shows the $Sc_3N$ moiety situated within the $C_{80}$ fullerene cage. While trimetallic nitride endohedral metallofullerenes are formed within $C_{80}$ carbon cages, the trimetallic nitride may be formed in other sized fullerene cages such as $C_{68}$ and $C_{78}$. FIG. 12 shows the structure of $Sc_3N@C_{68}$.

The method for making this family of metallofullerenes includes using a Krätschmer-Huffman generator, well known to one skilled in the art. This type of generator typically has a reaction chamber that can be easily evacuated and charged with a controlled pressure of an inert gas such as helium. The generator holds two electrodes within the reaction chamber and is able to apply a potential across the electrodes to produce an arc discharge.

The present method includes mounting a graphite rod, or other source of carbon, that has been filled with a mixture of a metal oxide and graphite in the reaction chamber. The metal oxide contains the metal to be encapsulated in the fullerene cage. The graphite rods are typically cored and filled with a mixture of metal oxide and graphite. The metal oxide may be the oxide of a trivalent metal. Preferably the metal oxide is the oxide of a rare earth metal or a group IIIB metal. Metal oxides may include, but are not limited to, $Er_2O_3$, $Ho_2O_3$, $Y_2O_3$, $La_2O_3$, $Gd_2O_3$, $Tm_2O_3$, or $Yb_2O_3$. The mixture of metal oxide and graphite may be from about 1% to about 5% metal oxide to graphite by weight. Typically, a 3% metal oxide to graphite loading will produce the desired trimetallic nitride endohedral metallofullerene.

When the encapsulation of more than one type of metal in the fullerene cage is desired, the cored graphite rod is filled with a mixture of metal oxides and graphite. The mixture of metal oxides should correspond to the desired metals and graphite. The metal oxides may be combination of trivalent metals in the form of oxides. Preferably, the metals are rare earth metal oxides or group IIIB metal oxides. The metal oxides may include, but are not limited to, $Er_2O_3$, $Ho_2O_3$, $Y_2O_3$, $La_2O_3$, $Gd_2O_3$, $Tm_2O_3$, or $Yb_2O_3$. The loading of each metal oxide may be from a 1% to about 5% metal oxide to graphite. Small amounts of cobalt oxide may be added to the mixture to enhance the formation of fullerenes. The addition of about 1 mg to about 425 mg of cobalt oxide may be added to the mixture. Typically, the addition of between about 75 mg and about 225 mg of cobalt oxide to the mixture will enhance the formation of the endohedral fullerenes. FIG. 7 shows the enhancement effect of adding a small amount of cobalt oxide to the metal oxide and graphite mixture.

Once the mixture is loaded into the cored graphite rod, the rod is place in the generator and the reaction chamber is evacuated. Helium is introduced into the reaction chamber at about 300 torr along with a small amount of nitrogen gas, about 1 to about 3 torr. A dynamic atmosphere ranging from about 300 ml/min to 1250 ml/min helium and about 20 ml/min to about 300 ml/min nitrogen gas may also be utilized. The ratio of helium to nitrogen is not critical. The trimetallic nitride endohedral metallofullerenes will be produced for a wide range of helium to nitrogen ratios, but yield of the metallofullerenes may tend to decrease as the amount of nitrogen approaches the amount of helium.

In order to form the trimetallic nitride endohedral metallofullerene, a source of nitrogen must be introduced into the reaction chamber. The source of nitrogen is preferably a nitrogen containing gas, but may include other nitrogen sources including but not limited to carbon nitrides and metal nitrides where the metal to be encapsulated is in nitride form.

A potential is applied across the electrodes resulting in an arc discharge. The arc discharge consumes the graphite rod and generates a wide range of carbon products generally referred to as soot. Within the soot is a wide range of fullerenes including the trimetallic nitride endohedral metallofullerenes.

Isolation of the trimetallic nitride endohedral metallofullerenes consists of using carbon disulfide or toluene to extract the soluble fullerenes from the soot. All members of the trimetallic nitride endohedral metallofullerenes, $Er_{3-n}Sc_nN@C_{80}$, $Ho_{3-n}Sc_nN@C_{80}$, $Y_{3-n}Sc_nN@C_{80}$, $Gd_{3-n}Sc_nN@C_{80}$ and $La_{3-n}Sc_nN@C_{80}$ where n=0–3, are extractable in carbon disulfide except $Yb_{3-n}Sc_nN@C_{80}$ and $Tm_{3-n}Sc_nN@C_{80}$ (n=0–3).

While the separation method is described for $A_{3-n}X_nN@C_{80}$ it is also applicable to other trimetallic nitride endohedral metallofullerenes such as $A_{3-n}X_nN@C_{68}$ and $A_{3-n}X_nN@C_{78}$. The carbon disulfide extract is typically filtered over a plug of glass wool to remove insoluble material. The extract is then subjected to a multi-stage chromatographic separation. The soluble extract is separated using an initial chromatographic separation stage that incorporates a pentabromobenzyl column using carbon disulfide as the mobile phase. One such column is available from Phenomenex Co., Torrance, Calif. In the second and third stages, a selective semi-preparative Trident-Tri-DNP (dinitorphenyl) column (Regis Chemical, Morton Grove, Ill.) may be utilized for isolation of $A_{3-n}X_nN@C_{80}$ with toluene as the solvent. A final separation stage utilizing a pentabromobenzyl column described above using $CS_2$ as the mobile phase may be used. The mobile phase elution rate is typically about 2 ml/min. In this manner, pure $A_{3-n}X_nN@C_{80}$ samples may be isolated.

In accordance with the present invention trimetallic nitride endohedral metallofullerenes having the general formula $A_{3-n}X_nN@C_{68}$, $A_{3-n}X_nN@C_{78}$, and $A_{3-n}X_nN@C_{80}$ are produced using the above described method. This family of trimetallic nitride endohedral metallofullerenes have properties that can find utility in conductors, semiconductor, superconductors, or materials with tunable electronic properties such as optical limiters, nonlinear optical devices, ferroelectrics. Trimetallic nitride endohedral metallofullerenes having encapsulated radioactive metals, such as Ho, may be used for medical applications such as radioactive tracers. These tracers may serve as fluorescent or optical tags. Further, trimetallic nitride endohedral metallofullerenes provide a new approach for surface dispersal for catalysts, coatings, and inks via a non-polar solvent (toluene, carbon disulfide, or 1,2-dichlorobenzene) or vacuum vaporization. The materials may be utilized directly as surface coatings or oxidized to the corresponding metal oxides.

The present invention is illustrated in the following examples. The examples are provided for illustration purposes and should not be construed as limiting the scope of the present invention.

EXAMPLE 1

Preparation of $Sc_3N@C_{80}$

A cored graphite rod was packed with a $Sc_2O_3$/graphite (3%/97%, weight/weight) mixture and loaded into a Krätschmer-Huffman generator. The packed graphite rod was vaporized in a dynamic helium atmosphere (300 torr) containing a small amount of nitrogen gas (1–3 torr). The vaporization produced $Sc_3N@C_{80}$ as shown by the negative ion (NI) mass spectra shown in FIG. 1c (1109 m/z). A pictorial representation of the structure of an empty $C_{80}$ cage and $Sc_3N@C_{80}$ is shown in FIGS. 1a and b.

EXAMPLE 2

Purification of $Sc_3N@C_{80}$

The reaction products of Example 1 were separated by first extracting the reaction products in carbon disulfide, $CS_2$ and filtering the soluble extract over a plug of glass wool. Next the soluble extract was separated using an initial chromatographic separation stage that incorporated a pentabromobenzyl column, (PBB, 25 cm×10 mm i.d., Phenomenex Co., Torrance, Calif.) with $CS_2$ as the mobile phase (2 ml/min). In the second and third stages, a selective semi-preparative Trident-Tri-DNP (di-nitorphenyl) column (Buckyclutcher, 25 cm×10 mm i.d., Regis Chemical, Morton Grove, Ill.) was utilized for isolation of the $Sc_3N@C_{80}$ with toluene as the solvent (2 ml/min). The final separation stage involved separation with the pentabromobenzyl column described above ($CS_2$ as the mobile phase, 2 ml/min). In this manner, pure $Sc_3N@C_{80}$ samples (2–4 mg) were separately isolated. Carbon disulfide solutions of $Sc_3N@C_{80}$ (~2 mg/ml solubility) appear as a reddish-brown color.

EXAMPLE 3

Characterization of $Sc_3N@C_{80}$

The 150 MHz $^{13}C$ NMR spectrum for purified $^{13}C$ enriched (~11% $^{13}C$ enrichment) $Sc_3N@C_{80}$ sample is shown in FIG. 1d. The spectrum consists of two resolved lines at 144.57 and 137.24 ppm with intensity ratio of 3/1 (60/20). This spectrum is consistent with a $C_{80}$ cage having $I_h$ symmetry. Fullerene carbon atoms which are at the intersection of three 6 membered rings (6MR) have been labeled as pyrene type sites and usually exhibit $^{13}C$ chemical shifts in the range of 130–138 ppm consistent with the peak at 137.24 ppm. Carbon atoms at the intersection of on 5 membered ring (5MR) and two 6MRs are termed corannulene sites and are usually in the range of 138–145 ppm consistent with the peak at 144.57 ppm. The observed $^{13}C$-$^{13}C$ spin-spin coupling pattern, ($J_{c-c}$=57.2 Hz) has the same satellite intensity for the doublets centered about the central peaks 144.57 and 137.24 ppm (3/1 intensity ratio). This is consistent with pyrene type carbons (137.24 ppm) bonded to 3 equivalent corannulene sites. The corannulene site (144.57 ppm) exhibits only one adjacent pyrene site. The magnitude of this scalar coupling interaction (57.2 Hz) is similar to values reported for other fullerene $sp^2$-$sp^2$ hybridized carbons. The $^{13}C$ NMR results suggest that internal motion of the $Sc_3N$ cluster yields a time-averaged electronic environment preserving overall $I_h$ symmetry for the carbon cage with the encapsulated $Sc_3N$ cluster not localized at specific internal bonding sites (at least on the NMR time scale at 295 K).

An ambient $^{45}Sc$ NMR spectrum for $SC_3N@C_{80}$ also exhibits a single symmetric line that is also consistent with a dynamic $Sc_3N$ cluster. A unique feature of the $C_{80}$-$I_h$ cage and the dynamic $Sc_3N@C_{80}$ structure is the absence of bonded carbon atoms between two different 5MRs as shown in FIGS. 1a and 1b. These sites are typically the most reactive in common fullerene cages ($C_{60}$, $C_{70}$, and $C_{84}$) and suggests a different reactivity pathway for $Sc_3N@C_{80}$.

It is generally thought that the electronic spectra of most endohedral metallofullerenes are generally dominated by features of the carbon cage rather than the encapsulated metals. The $Sc_3N$ cluster provides a significant perturbation of the carbon cage. The UV-Vis-NIR spectrum for $Sc_3N@C_{80}$ shown in FIG. 1e consists of significant absorption beyond 1000 nm and prominent peaks at 900 and 1140 nm. Assuming the absorption onset corresponds to the band-gap energy, the onset for $Sc_3N@C_{80}$ is approximately 1560 nm and corresponds to an estimate of 0.8 eV. In contrast, the absorption onset for $La_2@C_{80}$ is significantly higher in energy (~1000 nm, 1.3 eV) and consistent with a larger band-gap.

The x-ray photo-electron spectroscopy (XPS) spectrum for $Sc_3N@C_{80}$ is shown in FIG. 1f and has a characteristic absorption centered at ~400.9 eV for the $2p_{3/2}$ core level and a second peak due to spin-orbital coupling 4.8 eV higher energy than the $2p_{3/2}$ peak. These results are consistent with other scandium endohedrals. A small nitrogen peak is observed at 396.4 eV, the scandium and nitrogen XPS signal areas (corrected for relative sensitivities) provide agreement for a 3 to 1 ratio of atoms for the $Sc_3N$ cluster. The binding energy for the nitrogen peak of 396.4 eV compares favorably with the 396.2 eV value for scandium nitride.

The endohedral nature of $Sc_3N@C_{80}$ was confirmed by a single crystal X-ray diffraction study of $(Sc_3N@C_{80})$—$Co^{II}$(OEP)—1.5 chloroform—0.5 benzene, which was obtained by mixing a solution of $Sc_3N@C_{80}$ in benzene/carbon disulfide with a solution of $Co^{II}$(OEP) (OEP is the dianion of octaethylporphyrin) in chloroform. The resolved structure is shown in FIG. 2. The x-ray crystal data is as follows: $f_w$=1919.48, dark red parallelepiped, 0.02×0.02. 0.02 mm, monoclinic, space group $C_{2/m}$, a=25.142(5) b=15.246(3), c=19.459(3) Å, β=94.79(3), °V=7433(3) Å$^3$, λ=1.54178 Å, Z=4, $D_c$=1.715 Mg m$^{-3}$; μ(Cu—Kα)=6.012 mm$^{-1}$; $2\Theta_{max}$=113°; T=130 K; 9878 refl. Collected; 5138 independent ($R_{int}$=0.112) included in the refinement; no absorption correction performed; programs used for solution and refinement, SHELXS-97, Sheldrick, 1990; full-matrix least squares based on $F^2$, SHELXL-97; Sheldrick, 1998; 312 parameters, R1=0.2730, wR2=0.5932 for all data; R1=0.2244 computed for 3781 observed data (>2σ(I)). FIG. 2 shows the structure with the planar $Sc_3N$ unit clearly encapsulated within the $C_{80}$ cage. The $Sc_3N@C_{80}$ molecule is in close proximity but not covalently bonded to the $Co^{II}$(OEP) molecule, which makes face-to-face contact with another $Co^{II}$(OEP) moiety as seen in related compounds. The N—Sc distances, 2.011(19), 1.966(12) Å, are slightly shorter than the Sc—N bonds in amide compounds such as {$(HSiMe_2)_2N$}$_3$Sc(THF) that has an average Sc—N bond distance of 2.069 Å. In the crystal, the scandium ions face three pentagons within the $C_{80}$ cage.

The centrosymmetric electronegative nitrogen atom of the $Sc_3N$ cluster significantly alters other properties of the family of endohedral metallofullerenes. For example, it is well recognized that chromatographic retention behavior on non-polar chromatographic stationary phases (e.g., PYE, pyrenylethyl and PBB, pentabromobenzyl) is dominated by dispersion forces and to a lesser extent weaker induced dipole-dipole interactions. It has been established that the chromatographic retention parameter k', ($t_r/t_o$) is proportional to the polarizability and number of π electrons at the fullerene cage surface. Injection of $La_2@C_{80}$ onto a PBB stationary phase (toluene solvent), $La_2@C_{80}$ has a reported elution time corresponding to empty-cage $C_{88}$-$C_{90}$. Whereas, under similar conditions, $Sc_3N@C_{80}$ has an elution time corresponding to $C_{84}$-$C_{86}$. This decrease of approximately 4 π electrons at the fullerene cage surface of $Sc_3N@C_{80}$ suggests significant electron withdrawal from the carbon cage surface by the centrosymmetric nitrogen atom.

EXAMPLE 4

Preparation of $Sc_xEr_{3-x}N@C_{80}$ (x=0–3)

Figure 3A:
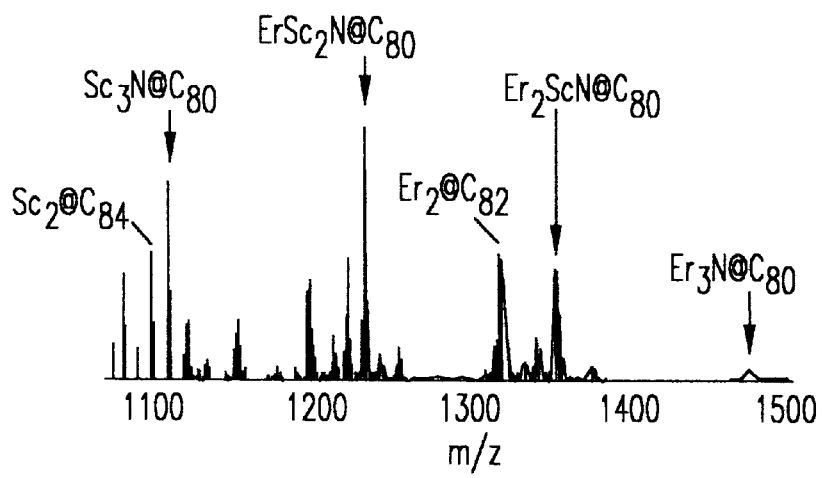

A cored graphite rod was packed with a $Er_2O_3$/$Sc_2O_3$/powdered graphite mixture and loaded into a Krätschmer-Huffman generator. Separate runs utilizing graphite rods packed with two different metal loadings were performed (1.5%/1.5%/97% and 3%/3%/94% weight $Er_2O_3$/weight $Sc_2O_3$/weight graphite). The packed graphite rod was vaporized in a dynamic helium atmosphere (300 torr) containing a small amount of nitrogen gas (1–3 torr). The vaporization produced all members of the $Sc_xEr_{3-x}N@C_{80}$ family as shown in the NI-DCI mass spectrum (FIG. 3a) of the chromatographic fraction after the first PBB/carbon disulfide separation stage. A pictorial cut out representation of the structures for $Sc_xEr_{3-x}N@C_{80}$ (x=0–3) are shown in FIG. 3b.

Figure 3C:
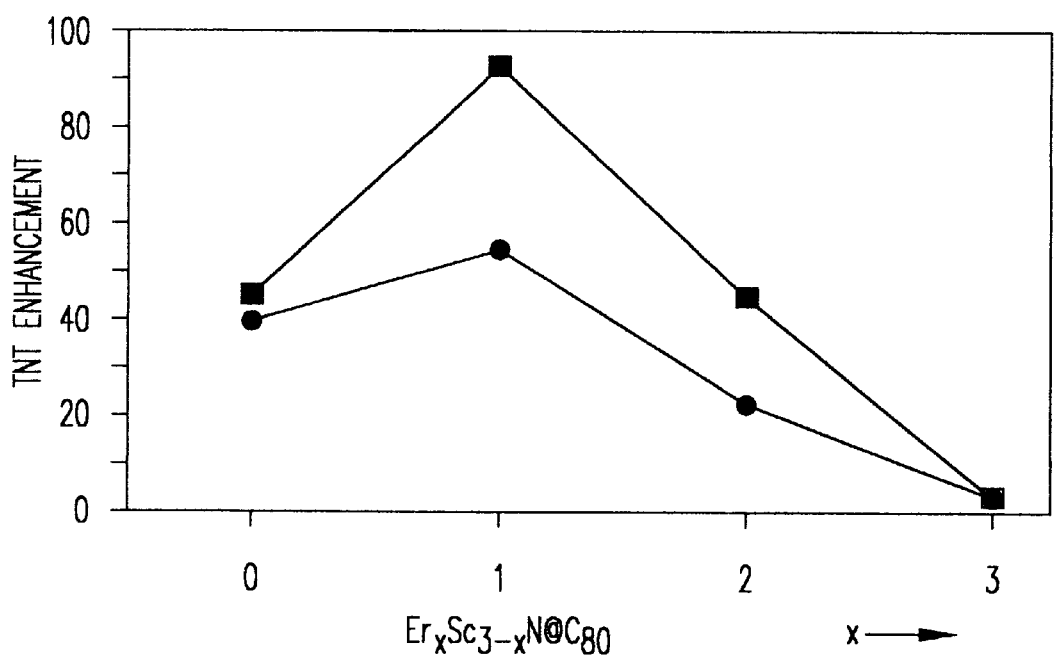
Figure 3B:
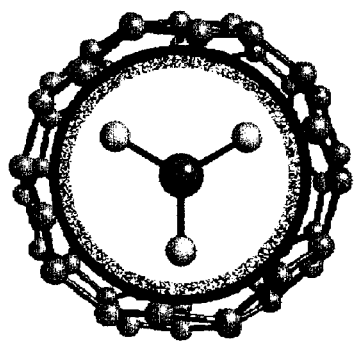
Figure 3B:
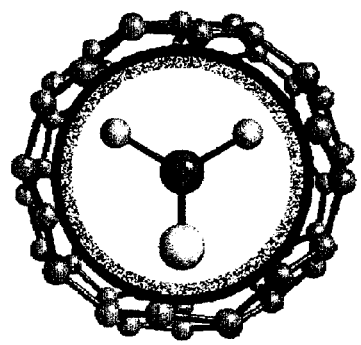
Figure 3B:
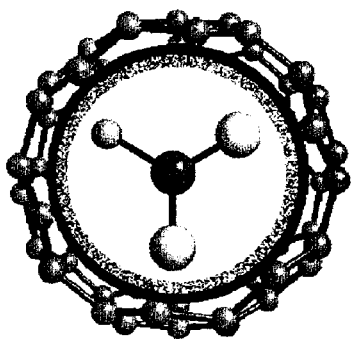
Figure 3B:
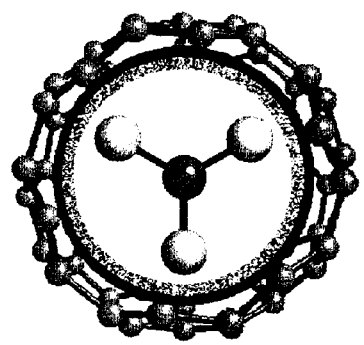

As shown in FIG. 3c, higher yields for $Sc_xEr_{3-x}N@C_{80}$ are obtained compared to $Sc_3@C_{82}$. The yields obtained from the mass spectral data are referenced to the well known trimetallic endohedral, $Sc_3@C_{82}$ which is not formed via the TNT process. The trimetallic nitride template (TNT) approach provides a route to new nanoscale materials with tunable electronic and dipolar properties.

EXAMPLE 5

Preparation of $A_{3-n}Sc_nN@C_{80}$ (n=0–3)

Cored graphite rods were packed with a mixture of $A_2O_3$ (A=Y, La, Gd, Ho, Yb, Tm, and Er), $Sc_2O_3$, powdered graphite, and cobalt oxide (100 mg–180 mg) keeping a constant A/Sc atomic ratio of 3%/2%. Each rod was loaded into a Krätschmer-Huffman generator and vaporized in a dynamic helium atmosphere (300 torr) containing a small amount of nitrogen gas (1–3 torr).

Figure 4:
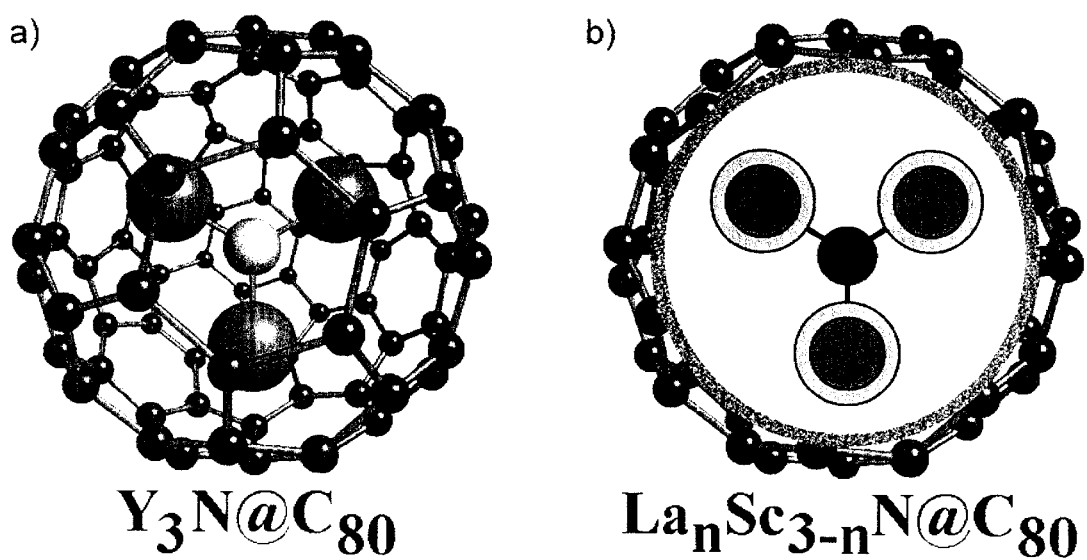

The soot from the vaporization of each rod was extracted with carbon disulfide and the soluble fraction was analyzed by negative-ion mass spectrometry. The vaporization produced all members of the $A_{3-n}Sc_nN@C_{80}$ (n=0–3). FIG. 4a shows a pictorial representation of the structure of $Y_3N@C_{80}$ and FIG. 4b shows a pictorial cut out representation of the structure for $La_{3-n}Sc_nN@C_{80}$ (n=0–3). The mass spectrum for A=Er, Y, Ho, and Sc are shown in FIGS. 8a–d respectively.

The yield enhancements for each of the $A_{3-n}Sc_nN@C_{80}$ (n=0–3) members are shown in FIG. 5 and the total TNT yield for each metal (A) as a function of ionic radii is illustrated in FIG. 6. This data shows the higher yield advantage for $A_3N$ cluster formation of Group III-B and rare earth metals by the TNT process relative to the non-TNT members and empty cages. As shown in FIG. 5, the yield enhancement form $Sc_3N@C_{80}$ ranges from 4–20 relative to the usually prominent non-TNT $Sc_2@C_{84}$ normally formed under non-TNT conditions (absence of $N_2$). As shown in FIGS. 5 and 6 large increase in yield is shown for Ho and Er with minor increases for Yb and Tm. Further, the effect of using cobalt oxide to facilitate formation of the trimetallic nitride endohedral fullerenes is illustrated in FIG. 7.

Without intending to be bound by theory, it appears that the group IIIB and rare earth trimetallic nitride template (TNT) formation for the $A_3N$ cluster in the $C_{80}$ cage is governed by a) an optimum $A_3N$ cluster size where element A has an ionic radius below about 0.095 nm, and b) the trivalent character of the encapsulated metal ions.

EXAMPLE 6

Preparation of $A_{3-n}Sc_nN@C_{68}$ (n=0–3)

Cored graphite rods were filled with 180 mg CoO in a mixture of 2% $Sc_2O_3$/3% $A_2O_3$/95% graphite powder (weight/weight) where A is Sc, Yb, Tm, Er, Ho, Gd, La, or Y. The filled rods were vaporized in a Krätschmer-Huffman type fullerene generator under a dynamic atmosphere of He (1250 ml/min) and $N_2$ (20 ml/min).

Figure 9A:
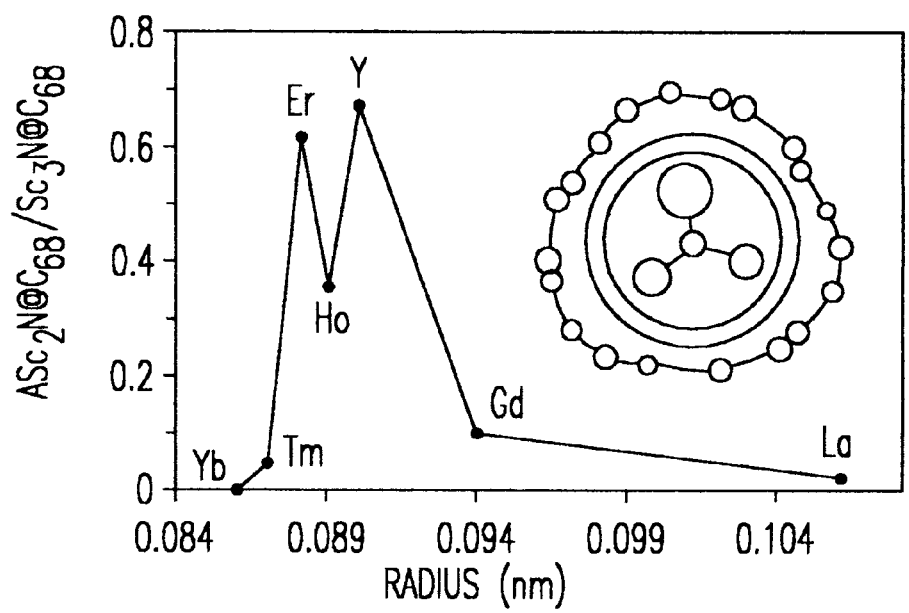
Figure 9B:
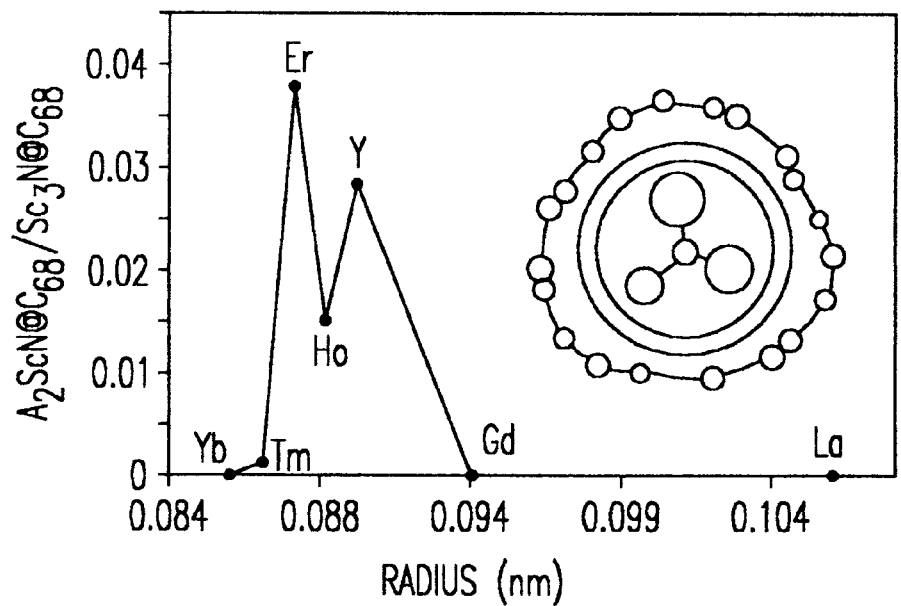

The resulting soot was extracted with cold $CS_2$ to yield a soluble extract. The extract was separated using the three-stage high pressure liquid chromatography technique described in Example 2 above. The chromatographic fraction corresponding to empty-cage elution from $C_{72}$-$C_{78}$ soluble fraction was analyzed by negative-ion mass spectrometry. FIGS. 9a and 9b show the relative yields of $ASc_2N@C_{68}$ and $A_2ScN@C_{68}$ compared to $Sc_3N@C_{68}$.

When A was Sc, the reaction product $Sc_3N@C_{68}$ was purified by injecting the extract into a pentabromobenzyl, PBB column (25 cm×10 mm, Phenomenex Co., Torrance, Calif. USA) to obtain a chromatographic fraction consisting primarily of $C_{76}$, $C_{78}$, and $Sc_3N@C_{68}$. Subsequent injection of this fraction into a Buckyclutcher column (25 cm×10 mm, Regis Chemical, Morton Grove, Ill. USA) yielded a sample of >95% pure $Sc_3N@C_{68}$. A final re-injection into the PBB column resulted in a highly purified (>99%) sample of $Sc_3N@C_{68}$. FIG. 10 a shows the NI-DCI mass spectrum for purified $Sc_3N@C_{68}$. The characteristic colors of $Sc_3N@C_{68}$, $Sc_3N@C_{78}$, and $Sc_3N@C_{80}$ are indigo, olive-green, and reddish-brown, respectively when dissolved in carbon disulfide.

EXAMPLE 7

Characterization of $Sc_3N@C_{68}$

The 121.5 MHz $^{45}Sc$ NMR spectrum for $Sc_3N@C_{68}$ in $CS_2$ is shown in FIG. 10b. The $^{45}Sc$ NMR for $Sc_3N@C_{68}$ exhibits a single symmetric peak in carbon disulfide at 296 K with a $^{45}Sc$ MNR linewidth of about 6560 Hz. On the $^{45}Sc$ NMR timescale, the results for $Sc_3N@C_{68}$ suggest that the three Sc atoms are equivalent at this temperature and are consistent with a molecule having three-fold symmetry.

The 150 MHz $^{13}C$ NMR spectrum for $Sc_3N@C_{68}$ in $CS_2$ is shown in FIG. 10c. The spectrum consists of a total of 12 resolved lines ranging from ~137 to 158.5 ppm with 11 lines of nearly equal intensity and 1 line, ⅓ intensity (136.87 ppm) that is the most shielded. The $^{13}C$ chemical shift range provides insight regarding the carbon structural network for $Sc_3N@C_{68}$.

Even for endohedral metallofullerenes the $^{13}C$ NMR spectra regions usually exhibit only minor shifts. Carbon atoms which are at the intersection of three 6 membered rings (6MR) have been labeled as pyrene type sites and typically exhibit $^{13}C$ chemical shifts in the range of 130–138 ppm. For example, the symmetry axis (1×2) carbons for the structure shown in FIG. 12 should reflect pyrene sites. Additionally, 2 of the remaining spectral lines in this region (137–138 ppm) can be ascribed to pyrene sites. Carbons at the intersection of one 5 membered ring (5MR) and two 6MR's are termed corannulene sites and are usually in the range of 138–145 ppm. The $^{13}C$ NMR spectrum exhibits 4 lines in the region of 137.6–143.55 ppm with corannulene type sites which is consistent with the structure shown in FIG. 12. A region of considerable curvature on a carbon fullerene surface occurs at the intersection of a 5MR and two 6MR which is further bonded to another 5MR. These carbons have been termed pyracylene sites and are usually more deshielded (145–151 ppm). There are 4 carbon signal (145.51, 147.41, 149.51 and 150.40 ppm) in this region of the spectrum, but there is only 1 pyracylene site for the structure shown in FIG. 12. Overlap of these latter spectral regions occur for many empty-cage fullerenes (e.g., corannulene and pyracylene ranges), but overlap with the pyrene region is usually less frequent. The $^{13}C$ NMR spectra for empty-cage fullerenes (e.g., $C_{60}$, $C_{70}$, and $C_{84}$) and endohedral metallofullerenes (e.g., $Sc_2@C_{84}$) do not generally exhibit peaks shifted downfield. This represents one of the unique features of the $^{13}C$ NMR spectrum for $Sc_3N@C_{68}$ where one spectral line (158.49 ppm) is significantly shifted down field from 151 ppm. This indicates that the carbons are not pyrene, corannulene, or pyracyene sites, but rather a new carbon site on the fullerene cage for $C_{68}$.

For a $C_{68}$ cage, the spiral algorithm (Fowler and Manolopoulos, An atlas of fullerenes, Oxford Univ. Press, Oxford 1995 herein incorporated by reference) finds 6332 distinct classical fullerenes, but only 23 support a $C_3$ axis consistent with the observed single symmetric $^{45}Sc$ NMR line observed in solution. Only 11 of these structures are consistent with the 12 $^{13}C$ NMR spectral lines (11×6, 1×2) observed in FIG. 10c. The 11 structures are shown in FIG. 11. Each fused pentagon pair (pentalene) has an energy penalty of 70–90 kj/mol, only two candidate structures have a minimum number pentagon pairs ($N_p=3$). Only one $C_{68}$ cage isomer (6140) is significantly stabilized at the density function tight binding (DFTB) semiempirical computational level. These calculations suggest increasing stability for isomer 6140 in progressing from a neutral $C_{68}$ cage to a cage supporting 6 additional electrons $(C_{68})^{-6}$. Isomer 6140 is 240 kj/mol more stable than the next most stable isomer 6275 for a $(C_{68})^{-6}$. Figure shows a structure for $Sc_3N@C_{68}$ consistent with the above data and observations.

The ultaviolet-visible-near infrared electronic spectrum for $Sc_3N@C_{68}$ is shown in FIG. 10d. The visible region for the $Sc_3N@C_{68}$ species consisting of two discrete minima (435 and 480 nm) and two local maximia (570 and 610 nm) that are consistent with the visual indigo color observed for $Sc_3N@C_{68}$. If the absorption onset reflects the HOMO/LUMO band-gap, the absorption onset for $Sc_3N@C_{68}$ is near 1300 nm (0.95 eV) and suggests a relatively small band gap. This value is in fair agreement with the DFTB values computed for $(C_{68})^{-4}$ and $(C_{68})^{-6}$, 0.72 and 1.28 eV respectively.

The chromatographic behavior of these TNT family members provides further insight regarding the charge distribution and polarity of these species. Less polar chromatographic stationary phases, such as PBB phases, exhibit weaker induced dipole-dipole interactions and dispersion forces and chromatographic retention times are proportional to the polarizability and number of π electrons on the fullerene cage surface. $Sc_3N@C_{68}$, $Sc_3N@C_{78}$, $Sc_3N@C_{80}$ have elution time when injected onto a PBB chromatographic column (carbon disulfide solvent) corresponding to empty-cages $C_{74}$-$C_{75}$, $C_{82}$-$C_{83}$, and $C_{84}$-$C_{85}$ respectively. Since the central electronegative nitrogen atom in these endohedrals is expected to exhibit significant electron withdrawal from the Sc atoms toward the cage center, significantly reduced π electron density (4–5 π electrons) is apparently transferred to the cage surface for $Sc_3N@C_{78}$ and $Sc_3N@C_{80}$. Whereas, the chromatographic retention data suggests 6–7 π electrons are transferred from the $Sc_3N$ cluster to the spheroidal carbon surface of $Sc_3N@C_{68}$. This suggests the importance of other retention mechanisms (including dipole-dipole) besides the transfer of π electrons to the carbon cage. The encapsulation of a four atom molecular cluster in a relatively small high symmetry carbon cage of only sixty eight carbon atoms represents a clear exception to the isolated pentagon rule (IPR) for fullerene formation.

It will therefore be readily understood by those persons skilled in the art that the present invention is susceptible to broad utility and application. Many embodiments and adaptations of the present invention other than those herein described, as well as many variations, modifications and equivalent arrangement, will be apparent from or reasonably suggested by the present invention and the foregoing description thereof, without departing from the substance or scope of the present invention.

Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims and the equivalents thereof.

What is claimed is:

1. An endohedral metallofullerene having the formula:

wherein:
A is a metal;
X is a second metal;
n is an integer from 0 to 3; and
m is an even integer from about 60 to about 200.

2. The metallofullerene of claim 1 wherein X is a trivalent metal and has an ionic radius below about 0.095 nm.

3. The metallofullerene of claim 2 wherein A is a trivalent metal and has an ionic radius below about 0.095 nm.

4. The metallofullerene of claim 1 wherein m is from about 60 to about 100.

5. The metallofullerene of claim 4 wherein m is about 68.

6. The metallofullerene of claim 4 wherein m is about 78.

7. The metallofullerene of claim 4 wherein m is about 80.

8. The metallofullerene of claim 1 wherein:
A is selected from the group consisting of Scandium, Yttrium, Lanthanum, Gadolinium, Holmium, Erbium, Thulium, and Ytterbium; and
X is selected from the group consisting of Scandium, Yttrium, Lanthanum, Gadolinium, Holmium, Erbium, Thulium, and Ytterbium.

9. The metallofullerene of claim 8 wherein X is Scandium.

10. The metallofullerene of claim 9 wherein A is selected from the group consisting of Erbium, Holmium, Scandium and Yttrium.

11. The metallofullerene of claim 10 wherein A is Erbium.

12. The metallofullerene of claim 10 wherein A is Holmnium.

13. The metallofullerene of claim 10 wherein A is Yttrium.

14. The metallofullerene of claim 1 wherein A is selected from the group consisting of a rare earth element and a group IIIB element.

15. The metallofullerene of claim 14 wherein X is selected from the group consisting of a rare earth element and a group IIIB element.

16. A method for making an endohedral metallofullerene comprising:
charging a reactor with a first metal, carbon, and nitrogen; and
reacting the nitrogen, the first metal, and the carbon in the reactor to form an endohedral metallofullerene.

17. The method of claim 16 wherein:
the nitrogen is introduced in the reactor in the form of nitrogen gas; and
the first metal and the carbon are introduced in the reactor in the form of a rod filled with a mixture of a first metal oxide and graphite wherein the first metal oxide is an oxide of the first metal.

18. The method of claim 17 wherein the first metal is selected from the group consisting of a rare earth element and a group IIIB element.

19. The method of claim 18 wherein the first metal is selected from the group consisting of Scandium, Yttrium, Lanthanum, Gadolinium, Holmium, Erbium, Thulium, and Ytterbium.

20. The method of claim 18 wherein the mixture comprises from about 1% to about 5% first metal oxide by weight.

21. The method of claim 20 wherein the mixture comprises about 3% first metal oxide by weight.

22. The method of claim 17 wherein reacting the nitrogen, carbon, and first metal further comprises vaporizing the carbon and the first metal in the presence of the nitrogen.

23. The method of claim 17 wherein the mixture further comprises from about 1 to about 450 mg of cobalt oxide.

24. The method of claim 17 wherein the mixture further comprises from about 75 to about 225 mg of cobalt oxide.

25. The method of claim 16 wherein the first metal has an ionic radius below about 0.095 nm.

26. The method of claim 25 wherein the first metal is a trivalent metal.

27. The method of claim 16 wherein the nitrogen is selected from the group consisting of carbon nitrides and metal nitrides wherein the metal nitride contains the first metal.

28. A method for making an endohedral metallofullerene comprising:

charging a reactor with a first metal, a second metal, carbon, and nitrogen; and reacting the nitrogen, the first metal, the second metal, and the carbon in the reactor to form an endohedral metallofullerene.

29. The method of claim 28 wherein:

the nitrogen is introduced in the reactor in the form of nitrogen gas; and the first metal, the second metal, and the carbon are introduced in the reactor in the form of a rod filled with a mixture of a first metal oxide, a second metal oxide, and graphite wherein the first metal oxide is an oxide of the first metal and the second metal oxide is an oxide of the second metal.

30. The method of claim 28 wherein:

the first metal is selected from the group consisting of a rare earth element and a group IIIB element; and the second metal is selected from the group consisting of a rare earth element and a group IIIB element.

31. The method of claim 29 wherein:

the first metal is selected from the group consisting of Scandium, Yttrium, Lanthanum, Gadolinium, Holmium, Erbium, Thulium, and Ytterbium; and the second metal is selected from the group consisting of Scandium, Yttrium, Lanthanum, Gadolinium, Holmium, Erbium, Thulium, and Ytterbium.

32. The method of claim 30 wherein the mixture comprises from about 1% to about 5% first metal oxide by weight and from about 1% to about 5% second metal oxide by weight.

33. The method of claim 31 wherein the mixture comprises about 3% first metal oxide and about 2% second metal oxide by weight.

34. The method of claim 28 wherein the first and second metals have an ionic radius below about 0.095 nm.

35. The method of claim 34 wherein the first and second metals are trivalent metals.

36. The method of claim 28 wherein reacting the nitrogen, carbon, first metal and second metal further comprises vaporizing the carbon, first metal and second metal in the presence of the nitrogen.

37. The method of claim 29 wherein the mixture further comprises from about 1 to about 450 mg of cobalt oxide.

38. The method of claim 29 wherein the mixture further comprises from about 75 to about 225 mg of cobalt oxide.

39. The method of claim 28 wherein the nitrogen is selected from the group consisting of carbon nitrides and metal nitrides wherein the metal nitride contains the first metal.

* * * * *